Figure 1:
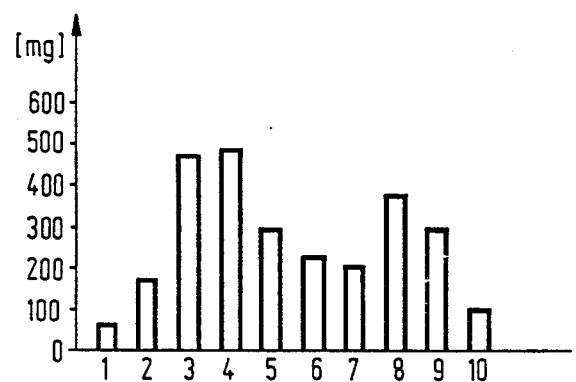

United States Patent [19]

Rembold et al.

[11] Patent Number: 4,902,713
[45] Date of Patent: Feb. 20, 1990

[54] AZADIRACHTIN-LIKE COMPOUNDS AND INSECT-DESTROYING AGENTS CONTAINING THEM

[75] Inventors: Heinz Rembold; Hans Forster, both of Munich, Fed. Rep. of Germany

[73] Assignee: Max-Planck-Gesellschaft zur Foederung der Wissenschaften e.V., Goettingen, Fed. Rep. of Germany

[21] Appl. No.: 146,820

[22] Filed: Jan. 22, 1988

[30] Foreign Application Priority Data

Jan. 26, 1987 [DE] Fed. Rep. of Germany ....... 3702175

[51] Int. Cl.$^4$ .................... A01N 43/16; C07D 317/70
[52] U.S. Cl. ..................................... 514/453; 549/383
[58] Field of Search ......................... 549/383; 514/453

[56] References Cited

PUBLICATIONS

"Natural Pesticides from the Neem Tree": Islam, pp. 263-290; Dreyer, pp. 435-443; Ahmed et al. pp. 565-580 (1984).
Butterworth et al., Chem. Comm., 1968, 23.

Primary Examiner—Nicky Chan
Attorney, Agent, or Firm—Felfe & Lynch

[57] ABSTRACT

The present invention provides compounds of the general formula:

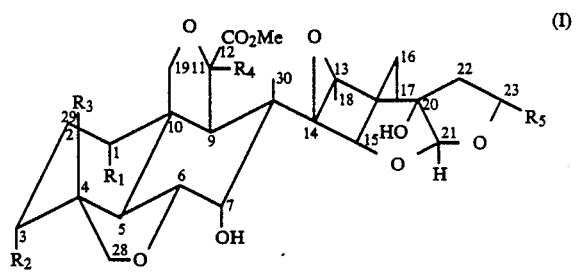

wherein $R_1$ is a hydroxyl group or an acyl radical of a straight-chained or branched, saturated or, when $R_2$ is an acyl radical other than an acetyl radical and/or $R_4$ is a hydrogen atom and/or $R_5$ is a hydrogen atom or an alkoxy radical, unsaturated monocarboxylic acid containing up to 10 carbon atoms, $R_2$ is a hydroxyl group or an acyl radical of a straight-chained or branched, saturated or, when $R_1$ is an acyl radical and/or $R_4$ is a hydroxyl group and/or $R_5$ is a hydrogen atom or an alkoxy radical, unsaturated monocarboxylic acid containing up to 10 carbon atoms, $R_3$ is an acetyl or methyl radical, $R_4$ is a hydrogen atom, a hydroxyl group or an acetyl radical and $R_5$ is a hydrogen atom, an alkoxy radical containing up to 6 carbon atoms (not only in the α- but also in the β-position) or an additional bond to C22.

The present invention also provides insect-destroying agents containing these compounds.

3 Claims, 1 Drawing Sheet

AZADIRACHTIN-LIKE COMPOUNDS AND INSECT-DESTROYING AGENTS CONTAINING THEM

The present invention is concerned with new azadirachtin-like compounds from the kernels of the nuts of the neem tree, the preparation of insect-destroying agents from a neem nut extract and insect-destroying agents which contain the azadirachtin-like compounds.

For about 100 years, insects have been combated by the use of insecticides. The best known insecticides of the new generation are the chlorinated hydrocarbons, such as DDT, aldrin and lindan. However, these compounds are also toxic for humans. In addition, they cause great ecological damage because they are only slowly broken down. In recent years, many kinds of insects have developed resistances against toxic insecticides and can, therefore, no longer be attacked with the compounds previously used. About 400 kinds of insects are today more or less resistant to the previously used insecticides.

This formation of resistance requires the development of new materials with which insects can still be combated. The new insecticides must be ecologically acceptable and also be non-toxic for other kinds of animal life. For many years and especially in developing countries, attempts have been made to obtain insecticides from the plant kingdom. As long ago as 1690, tobacco extracts, the active principle of which is nicotine, have been used in England for killing sucking insects. The rotenoid group of compounds, which occurs in the roots of *Derris elliptica*, is also effective against many insects but is almost harmless for warm-blooded animals.

To the most modern insecticides which can at present be used belong pyrethrum from *Chrysanthemum cinerariaefolium* and the pyrethroids.

Another plant from which insecticides could be developed is the neem tree, which is widely spread in India and East Africa. The neem tree is only attacked by a few insects. This has aroused the interest of many insect research workers and many component materials of this tree have been isolated. Some of them have feeding- and growth-inhibiting actions on insects, the most effective of these compounds being azadirachtin.

Insect growth inhibitors are substances which change the growth or certain developmental processes in insects. Most of the insecticides at present known, for example DDT, aldrin and pyrethrum, act in this manner. These substances are specific for insects since, in the case of insects, most growth and developmental processes take place in a way different from that of other organisms. Thus, the larva-larva, larva-pupa and pupaadult moulting is controlled, inter alia, by the moulting hormone ecdysone. The nature of the moulting is determined by the juvenile hormone (JH) concentration. Most of the insect growth inhibitors at present known act against the interplay of the two insect hormones ecdysone and juvenile hormone.

In the case of almost all insects, there are differences in the population density which depend upon the time of the year or upon the agricultural state of the attacked area. Therefore, with growth inhibitors, it is possible to prevent the population increase of the next generation.

There are various types of insect growth inhibitors:

(a) Juvenile hormones

Pest control with regulators, for example hormones, can only be successful when, in the life of the insect, there is a time in which the absence of this substance is important. This is so in the case of JH. However, JH cannot be widely used because the structure is too complicated for it to be produced with economically acceptable costs. Furthermore, juvenile hormones are labile compounds and also for this reason cannot be used on the field.

(b) Moulting hormones

These hormones are needed in the life of the insect in order to bring about moulting to the next larval stage. However, the moulting hormones ecdysone and 20-hydroxyecdysone have a steroidal structure which can only be synthesised with difficulty and expensively. Furthermore, many human hormones have a structural similarity with ecdysone. Therefore, an ecdysone analogue used over a large area could also be harmful for humans.

(c) Hormone antagonists

An inhibition of hormone activities is harmful for developing insects. The best known anti-juvenile hormone is precocene. In some insects, it brings about a precocious metamorphosis and prevents egg development in adult animals. Other hormone antagonists include, for example, piperonyl butoxide, as well as certain azasteroids. These materials suppress the development and metamorphosis of the insects but some of these materials are also harmful for humans.

In India, Togo, Bangladesh and other countries, neem formulations have been tested in fields and the results have been published in "Natural pesticides from the neem tree and other tropical plants", 1984, ed. H. Schmutterer, K.R.S. Ascher, GTZ, Eschborn, p. 435 (M. Dreyer), p. 263 (B.N. Islam) and p. 565 (S. Ahmed et al.). It was shown that the insect feeding was reduced and the crop yield increased. However, this type of insect control can only be used in a limited area. The protection by the neem formulation is maintained for at most 14 days because the active materials are destroyed by environmental influences and the field must be sprayed again. These feed-inhibiting formulations can better be used for the protection of stored products, such as stored rice and maize.

With the help of a feed test on the desert grasshopper, Butterworth and Morgan (1968) were able to isolate from neem kernels the most strongly feedinhibiting substance which they called azadirachtin. (Butterworth, J. H. and Morgan, E. D., "Isolation of a Substance that Suppresses Feeding in Locusts", *Chem. Comm.* 1968, 23.) Furthermore, it was ascertained that azadirachtin brought about a growth disturbance in different holometabolic insects. The larval development up to the adult stage was reduced and mortality was observed in the pupa stage. Since the increase of weight of the treated insects corresponded to that of the control insects, a feed inhibition could be excluded. The action of azadirachtin on the larva-pupa and pupa-adult moulting was interpreted as being a disturbance of the moulting hormone pool. The growth-inhibiting action in the case of larvae, as well as the inhibition of egg development in the case of adult insects, was also observed in the case of a number of other insects.

Since the previously used insecticides are harmful either for humans or for the environment or are not particularly strong, it is an object of the present invention to provide compounds based on azadirachtin which do not display the above-mentioned disadvantages or only to a limited extent and especially to provide compounds with increased effectiveness and little harm for other animals and humans, as well as the use thereof as active materials in insect-destroying agents. The present invention is also concerned with the preparation of an insect-destroying agent from an extract of the kernels of the nuts of the neem tree.

Thus, according to the present invention, there are provided compounds of the general formula:

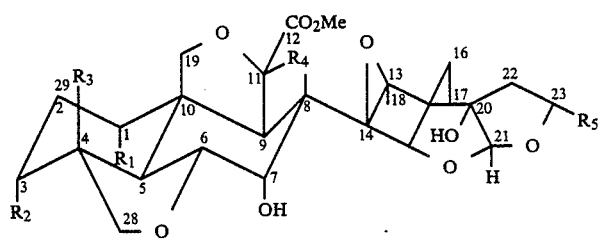

(I)

wherein $R_1$ is a hydroxyl group or an acyl radical of a straight-chained or branched, saturated or, when $R_2$ is an acyl radical other than an acetyl radical and/or $R_4$ is a hydrogen atom and/or $R_5$ is a hdrogen atom or an alkoxy radical, unsaturated monocarboxylic acid containing up to 10 carbon atoms, for example an acetyl, propionyl, n-butyryl, isobutyryl, n-valeroyl, isovaleroyl, n-caproyl or tigloyl radical, $R_2$ is also a hydroxyl group or an acyl radical of a straight-chained or branched, saturated or, when $R1$ is an acyl radical and/or $R_4$ is a hydroxyl group and/or $R_5$ is a hydrogen atom or an acyl radical, unsaturated monocarboxylic acid containing up to 10 carbon atoms, for example an acetyl, propionyl, n-butyryl, isobutyryl, n-valeroyl, isovaleroyl, n-caproyl or tigloyl radical, $R_3$ is an acetoxy or methyl radical, $R_4$ is a hydrogen atom, a hydroxyl group or an acetyl radical and $R_5$ is a hydrogen atom, an alkoxy radical containing up to 6 carbon atoms (not only in the α- but also in the β-position) or an additional bond to C-22. Thus, in the compounds of general formula (I), the carbon atoms 22 and 23 can contain not only a single but also a double carbon-carbon bond. FIG. 1 of the drawings is a weight diagram showing the results of column chromatography performed during the preparation of the azadirachtin compounds of this invention.

Figure 2:
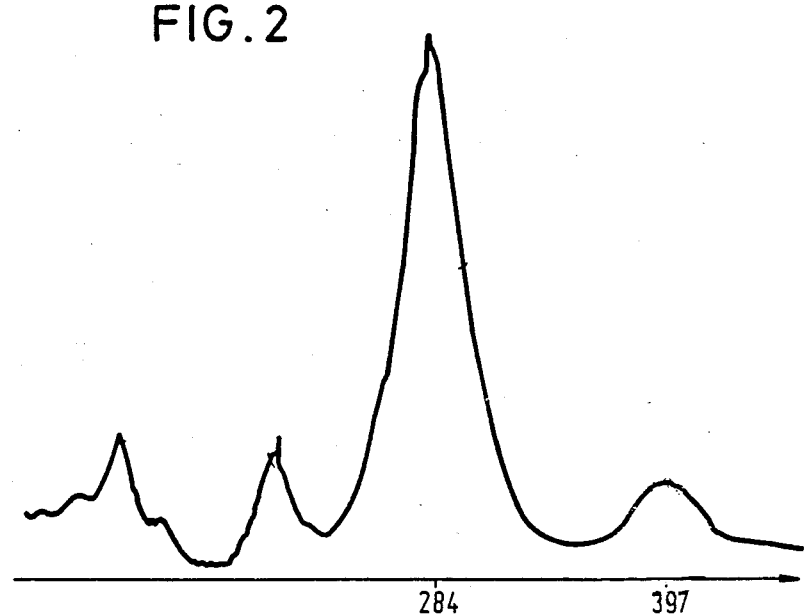

FIG. 2 shows a preparative HPLC chromatography of the crude azadirachtin A fraction obtained in the course of preparing the compounds of this invention.

Compounds are preferred in which $R_1$ and $R_2$ in the general formula are each a hydroxyl group, an acetyl radical or, under the above-mentioned conditions, a tigloyl radical, $R_4$ is a hydrogen atom or a hydroxyl group and $R_5$ is a hydrogen atom or an ethoxy radical or an additional bond to C-22. Most preferred are compounds in which $R_1$ and $R_2$ are each hydroxyl groups, for example 3-detigloyl-azadirachtin B. Preferred compounds include the following: azadirachtin F of the formula:

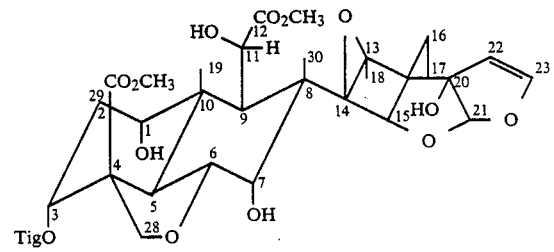

which is not included in general formula (I) but can be obtained in the course of preparing compounds of said formula; 22,23-dihydroazadirachtin A of the formula:

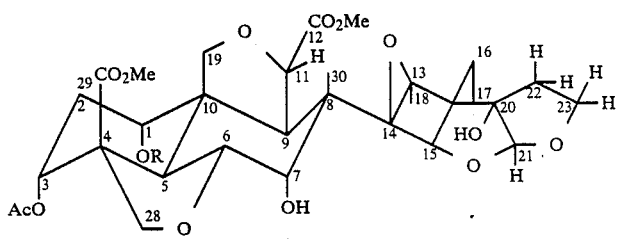

in which R is a tigloyl radical;
22,23-dihydroazadirachtin B of the formula:

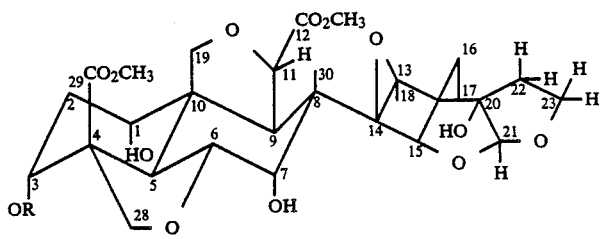

in which R is a tigloyl radical;
23-α-ethoxy-22,23-dihydroazadirachtin A of the formula:

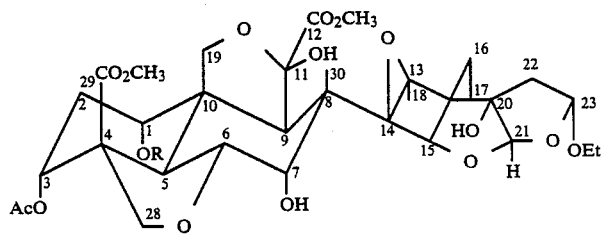

in which R is a tigloyl radical;
23-β-ethoxy-22,23-dihydroazadirachtin A of the formula:

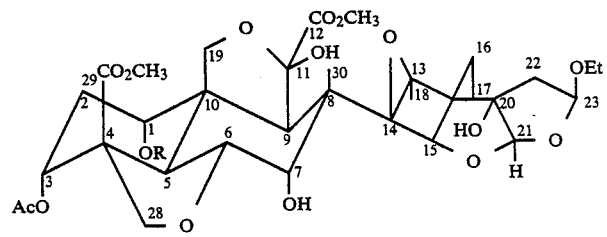

in which R is a tigloyl radical;
3-deacetyl-azadirachtin A of the formula:

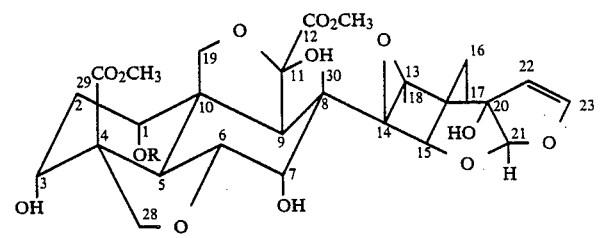

in which R is a tigloyl radical; and
3-detigloylazadirachtin B of the formula:

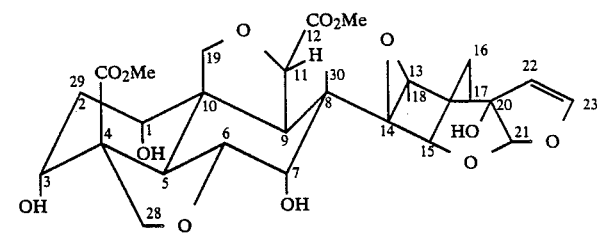

These compounds are either isolated from the nuts of the neem tree or are prepared from azadirachtin A and B by chemical derivatisation. The structures of these compounds were elucidated by spectroscopic methods and mainly by NMR.

In the case of the compounds deacetylazadirachtin A, detigloylazadirachtin B and azadirachtin F, the compounds only differ in the decalin system. In the case of all three compounds, the epoxide ring on C13–C14, the ketal function of C21, the dihydrofuran ring and the hydroxyl group on C7 are the same and presumably of importance for the effectiveness of the compounds. In the case of the above-mentioned seven specific compounds, the furan double bond is derivatised. In comparison with the parent compounds azadirachtin A and azadirachtin B, the activity of the compounds is the greatest when the hydroxyl groups on C1 and C3 are not esterified. In the same way, all compounds which have been derivatised on the furan double bond have a higher activity than the corresponding parent compounds azadirachtin A and B. In particular, the activity of the two ethoxy compounds are greatly increased. In the following Table 1, there is given activity test results for the various compounds in comparison with azadirachtin A and B.

TABLE 1

| compound | LC$_{50}$ (ppm) |
| --- | --- |
| azadirachtin A | 1.66 |
| azadirachtin B | 1.30 |
| deacetylazadirachtin A | 0.38 |
| detigloylazadirachtin B | 0.08 |
| azadirachtin F | 1.15 |
| 23α-ethoxy-22,23-dihydro-azadirachtin A | 0.74 |
| 23β-ethoxy-22,23-dihydro-azadirachtin A | 0.52 |
| 22,23-dihydroazadirachtin A | 1.26 |
| 22,23-dihydroazadirachtin B | 0.28 |

For this purpose, various concentrations of each compound were tested. Each concentration gave a mortality value. From these mortality values were calculated, with the computer programme of Noack and Reichmut (Mitt. Biol. Bundesanst. Land- und Forstwirtsch., No. 185, August, 1978), the lethal concentration for 50% of the insects (LC$_{50}$), the lethal concentration thereby being given in ppm. From Table 1, it can be seen tat detigloylazadirachtin B displays the highest insecticidal activity of the investigated compounds. However, all the other tested compounds have an activity which, in some cases, is far greater than the activity of the parent compounds azadirachtin A and B.

The process according to the present invention for the preparation of an insect-destroying agent from the crude extract of kernels of nuts of the neem tree is characterised in that the extract containing a natural azadirachtin mixture is saponified under such mild conditions that, in the case of the natural azadirachtins and of the derivatives thereof present, an ester group present on C1 and/or an ester group present on C3 is hydrolysed but in no case the epoxy group between C13 and C14. This can be achieved by saponification in a weakly basic solution at ambient temperature. The saponification is hereby preferably carried out in an aqueous solution of an alkali metal or alkaline earth carbonate, for example in 10% aqueous potassium carbonate solution. All azadirachtins and the derivatives thereof are thereby converted into the most strongly active form which, analogously to 3-detigloylazadirachtin B, have a hydroxyl group on C1 and C3. Other known mild methods of saponification can also be used.

Insect-destroying agents according to the present invention are characterised in that, as active material, they contain at least one compound which, as structural element, contains an azadirachtin structure of the general formula:

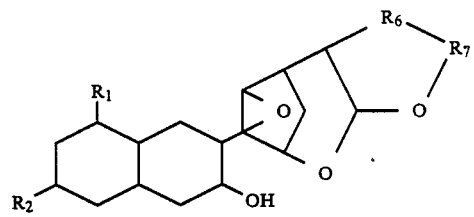

wherein $R_1$ is either a hydroxyl group or an acyl radical of a straight-chained or branched, saturated or, when $R_2$ is an acyl radical other than an acetyl radical and/or $R_6$, as well as $R_7$, are each a carbon atom with a hydrogen atom or an alkoxy radical as ligand, unsaturated monocarboxylic acid group containing up to 10 carbon atoms, for example an acetyl, propionyl, n-butyryl, isobutyryl, n-valeroyl, isovaleroyl, n-capronyl or tigloyl radical, $R_2$ is either a hydroxyl group or an acyl radical of a straight-chained or branched, saturated, or when $R_1$ is an acyl radical and/or $R_6$, as well as $R_7$, are each a carbon atom with a hydrogen atom or an alkoxy radical as ligand, unsaturated monocarboxylic acid containing up to 10 carbon atoms, for example an acetyl, propionyl, n-butyryl, isobutyryl, n-valeroyl, isovaleroyl n-caproyl or tigloyl radical, and $R_6$, as well as $R_7$, each represent a carbon atom with a hydrogen atom or an alkoxy radical containing up to 6 carbon atoms as ligand, whereby between $R_6$ and $R_7$ there can be either a single or double carbon-carbon bond, and, furthermore, optionally contain conventional carrier and/or dilution agents.

There are hereby preferred compounds nn which $R_1$ and $R_2$ both represent hydroxyl groups, acetyl radicals or, under the above-mentioned conditions, tigloyl radicals and $R_6$ and $R_7$ each represent a carbon atom with a hydrogen atom or an ethoxy radical as ligand or an additional bond to $R_7$ or $R_6$. Especially preferably, $R_1$ and $R_2$ are both hydroxyl groups. Other insect-destroying agents according to the present invention contain at least one compound according to the present invention.

By means of the compounds present in the insect-destroying agents according to the present invention, the development of insects, which was investigated, by way of example, on the bean beetle, is impaired from the $L_4$ stage up to the adult insect. Normally, the insects Pass through several stages of development when the growth is not disturbed. From the larva in the fourth stage there develops a prepupa which then passes into the pupa stage. From the pupa emerges the adult insect. After the administration of azadirachtin or derivatives thereof, various disturbances of the growth can be observed in these developmental stages:

(a) prolongation of the larva stage up to permanent larva,
(b) if a prepupa has developed, dehydration thereof,
(c) drying out of the normal pupa,
(d) development of a normal pupa but the insect is not able to remove the pupa covering and it dies from exhaustion,
(e) the adult insect emerges from the covering but has such deformations that it is not capable of living.

The individual insects only suffer from one of these growth disturbances. However, each disturbance suffices to suppress a normal development. Besides the growth-inhibiting action of the compounds according to the present invention, a feeding inhibition is also possible.

The following Examples are given for the purpose of illustrating the present invention:

EXAMPLE 1

Isolation of azadirachtin and subsequent derivatisation.

For the working up of 57 kg. neem nuts, the neem nuts are freed from the shells in a wheat dehulling device. The separation of the hull parts from the kernels takes place in a wind-sieving device. The hulls (30 kg.) do not contain any azadirachtin and are discarded. Further working up was continued with the kernels (27 kg.). In order to provide better conditions for the subsequent extraction, the neem nuts were ground with a flour mill. The oily powder obtained was extracted as quickly as possible in order to avoid enzymatic decomposition reactions. The 27 kg. of ground neem kernels were divided up into 5 portions. Each portion was stirred twice with 10 litres of technical grade hexane for 2 hours. Thereafter, it was filtered and the extracts of the individual portions were combined. After distilling off the solvent, there were obtained 12.0 kg. neem oil. The gas space in the 20 litre flask used was continuously flushed with air. In this way, an inflammable mixture could not be formed. 15 kg. of deoiled neem powder remained behind. This powder was divided up into 3 portions and extracted in the same apparatus, in each case twice with 10 litre amounts of technical acetone. The combined acetone dry extracts had a weight of 1670 g. An analysis with thin layer chromatography showed that azadirachtin was only contained in the acetone fraction. The combined acetone fractions were dissolved in methanol and mixed with 1500 g. of silica gel. The methanol was distilled off and the acetone fraction remained on the silica gel. For filtration, a column with a length of 30 cm. and a diameter of 10 cm. was filled with silica gel. The acetone fraction (1.6 kg.) on silica gel was divided up into 5 portions. Each portion was eluted on the abovementioned silica gel column with two different petroleum ether/ethyl acetate mixtures, first eluting with 4 litres of petroleum ether-/ethyl acetate (7:3 v/v) and then with 4 litres of petroleumether/ethyl acetate (1:4 v/v). The silica gel column was thereafter regenerated with methanol and could be used again. The main amount, namely 1.140 g. azadirachtin, was contained in the combined first fractions and a smaller amount, namely 170 g., was contained in the combined second fractions. A part of this small amount was extracted with methanol/ water/hexane (4:1:5 v/v/v), the methanol phase thereby containing the main amount of the azadirachtin (about 95%). Thereafter, the azadirachtin compounds were separated by column chromatography over a 300 mm. long column of 25 mm. diameter which was filled with 100 g. silicon dioxide-RP-8 material. The elution agent methanol/water (7:3 v/v) was best suited for this purpose. For each run, 7 g. of the methanol fraction of the second fraction from the preceding purification step were used. Fractions were taken right from the beginning.

Each fraction corresponded to 10 minutes of elution time (about 15 ml. of solvent). The fractions were freed from solvent, weighed and analysed by thin layer chromatography. FIG. 1 of the accompanying drawings shows a weight diagram of the column chromatography on RP-8-SiO$_2$. On the abscissae are plotted the fractions and on the ordinates the dry weights of the fractions: This weight diagram shows two maxima. The first maximum corresponds to azadirachtin A and the second maximum not to an azadirachtin B peak but rather another unknown compound. Azadirachtin B is enriched in fractions 6, 7 and 8.

The fractions around the two maxima were constituted by, in all, 8 portions. 15.5 g. azadirachtin A fraction, as well as 8.3 g. azadirachtin B fraction, were obtained. However, the azadirachtin A fraction still contained a large amount of azadirachtin B, whereas the azadirachtin B fraction still contained other substances in almost the same amount as azadirachtin B. Preparative HPLC was used in order to separate azadirachtin A and B. For this purpose, there was used a Latek column filled with silica gel-RP-18 material with a length of 540 mm. and an internal diameter of 54 mm. The separation was optimised. The flowthrough rate was 55 ml./minute with methanol/water (43:57 v/v) as elution agent. For each run, about 5 g. of the azadirachtin A fraction from the column chromatography on silica gel-RP-8 were applied to the column. Every 9 minutes, the receiver was changed at a volume of about 500 ml. The maximum of azadirachtin A was eluted after 284 minutes and the maximum of azadirachtin B appeared after 397 minutes. FIG. 2 of the accompanying drawings shows a preparative HPLC chromatography of the azadirachtin A fraction in the case of chromatography on RP-8. Pure azadirachtin A and azadirachtin B was only contained in the fractions round the peak maximum. Five further azadirachtins were also separated on a smaller scale in side fractions of the preparative HPLC with thin layer chromatography or semi-preparative HPLC. The various azadirachtin derivatives were prepared from azadirachtin A and azadirachtin B.

EXAMPLE 2

Isolation of azadirachtin F.

The substance was isolated from a polar fraction of the preparative HPLC. 20 mg. of this fraction were applied to two 0.5 mm. 20×20 cm. silicon dioxide plates and chromatographed with the elution agent chloroform/acetone (7:3 v/v). The band with $R_f$ 0.27 was scraped off. Yield: 4.50 mg. Analysis: elution agent: methanol/water (2:3 v/v); column 100×5 mm.; 3 μm RP-18 material. Azadirachtin F: RT 4.91 minutes (azadirachtin A 8.8 minutes).

EXAMPLE 3

Preparation of 22,23-dihydroazadirachtin A.

40.8 mg. azadirachtin A (5.67×10$^{31}$ $^5$ mole) were dissolved in 4 ml. ethyl acetate and 20 mg. platinum dioxide dihydrate were added thereto. The mixture was stirred and hydrogen passed therethrough for 75 minutes, the course of the reaction being monitored by HPLC. After the disappearance of the azadirachtin A peak, the reaction was discontinued and the reaction mixture centrifuged. The supernatant solution was evaporated and purified on silicon dioxide thin layer chromatography plates using the elution agent chloroform/acetone (7:3 v/v); $R_f$0.33. Yield: 28.2 mg. (69% of theory).

EXAMPLE 4

Preparation of 22,23-dihydroazadirachtin B.

95 mg. azadirachtin B (1.44×10$^{31}$ $^4$ mole) were dissolved in 7 ml. ethyl acetate, 45 mg. platinum dioxide dihydrate were added thereto and the mixture was stirred and hydrogen passed therethrough for 2 hours, whereafter the mixture was filtered and centrifuged. The supernatant was evaporated and purified by thin layer chromatography, using the elution agent diethyl ether/acetone (4:1 v/v); $R_f$ 0.37. Yield: 68 mg. (67% of theory).

EXAMPLE 5

Preparation of 23α-ethoxy-22,23-dihydroazadirachtin A and 23β-ethoxy-22,23-dihydroazadirachtin A.

30 mg. azadirachtin A ($4.2 \times 10^{-5}$ mole) were dissolved in 0.5 ml. chloroform and 120 μl. of acetylation solution (50 μl. acetyl chloride and 2 ml. chloroform) were added thereto. After 10 minutes, unreacted acetyl chloride was destroyed with water. The reaction mixture was neutralised with an aqueous solution of sodium bicarbonate and then extracted with chloroform. Subsequent purification took place by thin layer chromatography on 0.5 mm. silicon dioxide plates, using the elution agent chloroform/acetone (7:3 v/v), two main components being obtained:
1. $R_f$ 0.54: 23α-ethoxy derivative; yield 5.2 mg.
2. $R_f$ 0 24: 23β-ethoxy derivative; yield 2.4 mg.

In the case of using benzoyl chloride instead of acetyl chloride, only the 23α-ethoxy derivative was obtained, the reaction only being complete after standing overnight.

EXAMPLE 6

Preparation of 3-deacetylazadirachtin A.

15.8 mg. azadirachtin A ($2.2 \times 10^{-5}$ mole) were dissolved in 100 μl. methanol. To this solution were added three times 100 μl. amounts of a methanolic solution of sodium methylate (0.6 g. sodium in 50 ml. methanol). After each addition of 100 μl. methylate solution, there was a pause of 2 minutes and then a testing with HPLC whether azadirachtin A was still present. After the disappearance of azadirachtin A, the reaction mixture was neutralised with acetic acid, diluted with water and extracted with chloroform. The purification from by-products took place by semipreparative HPLC on a 20 cm. RP-18 column of 9 mm. internal diameter, using the elution agent methanol/water (2:3 v/v); detection at 215 nm; yield 2.4 mg. (15.2% of theory).

EXAMPLE 7

Preparation of 3-detigloylazadirachtin B.

20 mg. azadirachtin B ($3.0 \times 10^{-5}$ mole) were dissolved in 1 ml. methanol. 5 ml. of a 10% aqueous solution of potassium carbonate were then added thereto. After 12 hours, the reaction mixture was extracted with chloroform and the chloroform phase was evaporated and purified by thin layer chromatography using the elution agent chloroform/acetone (7:3 v/v); $R_f$ 0.13. Yield 5.2 mg. (26% of theory).

We claim:
1. Azadirachtin F of the formula in which Tig represents tigloyl.

2. An insect-destroying agent comprising, as active material azadirachtin F of the formula in which Tig represents tigloyl, and a carrier 3. A method for combatting insects which comprises applying to said insects in their developing stages, in sufficient amount to disturb their growth, azadirachtin F of the formula in which Tig represents tigloyl.

* * * * *

UNITED STATES PATENT AND TRADEMARK OFFICE
CERTIFICATE OF CORRECTION

PATENT NO. : 4,902,713

DATED : February 20, 1990

INVENTOR(S) : Heinz Rembold, et al

It is certified that error appears in the above-identified patent and that said Letters Patent is hereby corrected as shown below:

Col. 10, line 51 — change "(5.67 x $10^{31}$ $^5$ mole)" to -- (5.67 x $10^{-5}$ mole) --.

Col. 10, line 66 — change "1.44 x $10^{31}$ $^4$ mole)" to -- (1.44 x $10^{-4}$ mole) --.

Col 11, line 12 — change "4.2 x 10-5 mole)" to -- (4.2 x $10^{-5}$ mole) --.

Signed and Sealed this

Eleventh Day of February, 1992

Attest:

HARRY F. MANBECK, JR.

*Attesting Officer*     *Commissioner of Patents and Trademarks*